(12) United States Patent
Niazi

(10) Patent No.: US 6,555,118 B1
(45) Date of Patent: Apr. 29, 2003

(54) PHARMACEUTICAL PREPARATION FOR THE TREATMENT OF TOPICAL WOUNDS AND ULCERS

(76) Inventor: Sarfaraz K Niazi, 20 Riverside Dr., Deerfield, IL (US) 60015

(*) Notice: Subject to any disclaimer, the term of this patent is extended or adjusted under 35 U.S.C. 154(b) by 0 days.

(21) Appl. No.: 09/681,207

(22) Filed: Feb. 22, 2001

(51) Int. Cl.$^7$ .......................... A61K 35/78; A61K 7/00; A61K 7/48; A61K 7/26; A01N 63/00

(52) U.S. Cl. .................. 424/401; 424/725; 424/773; 424/774; 424/779; 424/93.7; 424/767; 424/78.06; 424/DIG. 13; 514/783; 514/844; 514/944; 514/945

(58) Field of Search ................ 424/401, 725, 424/773, 774, 779, 93.7, 767, 78.06, DIG. 13; 514/783, 844, 944, 945

(56) References Cited

U.S. PATENT DOCUMENTS 5,405,608 A * 4/1995 Xu ............................ 424/725
5,690,961 A * 11/1997 Nguyen ...................... 424/488
5,747,462 A * 5/1998 Fuentes ....................... 514/23

OTHER PUBLICATIONS

The International Cosmetic Ingredient Dictionary and Handbook, Seventh Edition, vol. 2, 1997, pp 1196 and 1241–1242.*

* cited by examiner

Primary Examiner—Frederick Krass
Assistant Examiner—Clinton Ostrup
(74) Attorney, Agent, or Firm—Welsh & Katz, Ltd.

(57) ABSTRACT

A pharmaceutical preparation for the treatment of wounds and ulcers in humans and animals and a method of preparation of the same are provided here. The composition consists of an alcoholic extract of Huangqin, Huanglian, Huangbai, Opuntia, Dilong, and β-sitosterol (from Soybean extract), in a vegetable oil-wax base, from where the alcohol is essentially removed by evaporation. The composition is used as a topical ointment for the treatment of wounds in its preferred embodiment. Wounds, in particular those occurring in the skin as second and third degree burns, stasis ulcers, trophic lesions, such as decubitus ulcers, diabetic ulcers, surgical wounds, severe cuts, diaper rash, cracked nipples and abrasions which are commonly resistant to the natural healing process, may be treated with this composition. The application of this combination to wounds greatly accelerates the rate of healing and reduces scarring as the mechanism of action proposed here involves regeneration of skin through stimulation of stem cells that allows healing without substantial scar formation.

5 Claims, No Drawings

PHARMACEUTICAL PREPARATION FOR THE TREATMENT OF TOPICAL WOUNDS AND ULCERS

DETAILED DESCRIPTION

Wound healing involves a complex but orderly sequence of cellular events that culminates in the restoration of structural integrity of tissue. The orderly influx of inflammatory cells, proliferation of stromal elements, in-growth of blood vessels, and production of an extra-cellular matrix are essential for rapid and efficient healing. Maximum tissue strength is achieved through the regulated remodeling and maturation of the extra-cellular matrix. Tissue repair is regulated in part by cells at the wound site that control the local production of growth factors, including transforming growth factor beta. Wound healing begins with a repair cascade, which culminates in the formation of new granulation tissue.

Cutaneous ulcers are a common, chronic problem and are primarily developed as pressure (decubital) sores. In addition to causing pain and discomfort and predisposing the patient to superficial and chronic infection, significant costs are associated with the treatment that is often long-term. Chronic ulcers may also arise as a result of chronic steroid therapy for autoimmune disease or atopic dermatitis as well as chemotherapy for cancer. These conditions and their treatment regimens may impair the normal wound healing process and often result in chronic ulcers. While the etiology of pressure sores or ulcers resulting from chronic steroid or chemotherapy may be different, the underlying manifestation is the lack of formation of granulation tissue and re-epithelialization of the defect. Depending on the health and background of the patient, these cutaneous open wounds and ulcers can persist chronically for extended periods of time. Each of these types of cutaneous open wounds and ulcers results in considerable discomfort to the patient and presents a continuing opportunity for even more serious infections or complications to occur. In addition to these common cutaneous open wounds and ulcers, a variety of other skin defects are known to occur in both animals and humans, including lacerations, perforations, wounds which are traumatic in origin, venous stasis ulcers, and other types of lesions.

These types of wounds also occur in other vertebrates such as birds and reptiles. The fundamental pathogenesis of wounds and processes for wound healing is similar for all vertebrates, and therefore the person of ordinary skill will realize that the methods and compositions of the present invention are useful for treating chronic wounds and ulcers in all vertebrates.

By "open wound" is meant any injury, which communicates with the atmosphere, by direct exposure. Open wounds include, but are not limited to, decubital ulcers, dehiscence wounds, acral lick dermatitis (acral lick granulomas in animals), lacerations, and wounds that are traumatic in origin. By "ulcer" is meant a break in the continuity of the epidermis with a loss of substance and exposure of underlying tissue. By "chronic cutaneous open wound or ulcer" is meant a cutaneous open wound or ulcer, which has shown resistance to completing the healing process. By "burn wounds" is meant a surface wound ranging from first to third degree burn and ranging from affecting 1% to 99% body surface area.

The cessation of blood flow to an ischemic lesion can be developed in a slow and gradual form such as in the case of decubitus ulcers and stasis ulcers, or may take place more acutely such as in thermo-radiation and chemical burns. In the absence of nutrition, the rate of fluid delivery of nutrients decreases bringing a progressive impairment in the viability of cells and tissues. This eventually leads to degeneration and death of the tissue and cells in a condition known as necrosis. Necrosis is generally accompanied by bacterial, fungal and/or viral contamination. As further pointed out in the aforementioned patent, treatment of exudative skin wounds with a starch hydrolysate dressing produces a greatly reduced bacteria count of an infected wound and inhibits infection of an uninfected wound. In addition, application of the starch hydrolysate to a wound or ulcer produces a film or semi-permeable membrane which allows edematous liquid to pass through while proteinaceous material is retained within the body, allowing reduction in the volume of exudate in relatively clean condition.

The process of wound healing consists of three phases during which the injured tissue is repaired, regenerated, and new tissue is reorganized into a scar. These three phases are classified as: a) an inflammation phase which begins from day 0 to 3 days, b) a cellular proliferation phase from 3 to 12 days, and c) a remodeling phase from 3 days to about 6 months. In the inflammation phase, inflammatory cells, mostly neutrophils, enter the site of the wound followed by lymphocytes, monocytes, and later macrophages. The neutrophils that are stimulated begin to release proteases and reactive oxygen species into the surrounding medium with potential adverse effects on both the adjacent tissues and the invading microorganisms. The oxygen species known to be released by the neutrophils are superoxide through the action of a plasma membrane-bound NADPH oxidase, hydrogen peroxide formed by action of dismutation of superoxide, and HOCl produced by the action of myeloperoxidase with hydrogen peroxide. The proliferative phase consists of laying down new granulation tissue, and the formation of new blood vessels in the injured area. The fibroblasts, endothelial cells, and epithelial cells migrate in the wound site. These fibroblasts produce the collagen that is necessary for wound repair. In reepithelialization, epithelial cells migrate from the free edges of the tissue across the wound. This event is succeeded by the proliferation of epithelial cells at the periphery of the wound. Research has also shown that reepithelialization is enhanced by the presence of occlusive wound dressings which maintain a moisture barrier. The final phase of wound healing, which is remodeling, is affected by both the replacement of granulation tissue with collagen and elastin fibers and the devascularization of the granulation tissue.

A large variety of treatment and modalities are available for the treatment of wounds and ulcers as described here. These range from applications of antibiotics, occlusive layers, bandages, poultices, mechanical devices that reduce evaporation of water and many others. However, all of these modalities have one drawback in common; they all enhance wound healing by supporting the body mechanisms to heal the wound. Unfortunately, the passive healing process results in much disappointment because the body may have compromised immunity or other body functions that may not work optimally. What is needed is a modality of treatment that will actively regenerate the skin, dermis and epidermis. In the invention described here, the specific composition actively promotes healing by stimulating stem cells that are present even in deep wounds and burns to regenerate the lost tissue.

Stem cells are by definition present in all self-renewing tissues. These cells are believed to be long-lived, have a great potential for cell division and are ultimately responsible for the homeostasis of steady-state tissues. Stem cells are normally slow cycling. They can, however, be induced to enter the proliferative pool in response to certain growth stimuli. When stem cells undergo occasional cell division, they give rise to more rapidly proliferating "transient amplifying cells" ("TA"). Stem cells possess many of the following properties: they are relatively undifferentiated, ultrastructurally and biochemically; they have a large proliferative potential and are responsible for the long term maintenance and regeneration of the tissue; they are normally "slow-cycling", presumably to conserve their proliferative potential and to minimize DNA errors that could occur during replication; they can be stimulated to proliferate in response to wounding and to certain growth stimuli; they are often located in close proximity to a population of rapidly proliferating cells corresponding to the transient amplifying cells ("TA") in the scheme of (1) stem cell to (2) TA cell to (3) terminally differentiated cell, and they are usually found in well protected, highly vascularized and innervated areas. Positive identification of stem cells has been difficult because, there are few known immunological or biochemical markers specific for epithelial stem cells. Since they are normally "slow-cycling", they cannot be labeled by single pulse administration of radioactive materials typically used to detect actively proliferating TA cells. The U.S. Pat. No. 5,756,094 to Lavker, et al., describes a method for identification of these cells by labeling these cells continuously to generate label-retaining cells (LRCs). Cotsarelis et al., J. Invest. Dermatol. 1989, 92(3) disclose a method to facilitate detection of LRCs based on the ability of slow-cycling cells to be recruited to proliferate in response to hyperplastic stimuli.

A number of growth factors have been reported to be useful for modulating stem cell activity. For example, cytokines such as Tumor Necrosis Factor (TNF), Epidermal Growth Factor (EGF), Transforming Growth Factor (TGF) and Interleukin-1 (IL-1) are believed to be useful. Because stem cells are normally slow cycling but proliferate rapidly upon inductive stimulation, they may be attractive targets for cytokines such as TNF. EGF has been shown to have broad biological effects. Furthermore, it has been shown to support growth during fetal development and accelerate re-epithelialization during wound healing. TGF-α has been shown to be involved in the regulation of both growth and differentiation of epithelial cells. IL-1 is known to induce proliferative activity in epidermal cells.

In this invention, an alcoholic extract of ingredients in dried powdered state consisting of Huangqin (baikal skullcap), Huanglian (rhizome of Chinese goldthread or rhizoma coptidis), Huangbai (cortex phellodendri), earthworm (Dilong), Cactus (opuntia ficus indica) in which each of the ingredients is preferably in an amount of about 5%, and in the range of 1.0 to 15% of the final amount of preparation and soybean concentrate as a source of β-sitosterol is used. In the foregoing assertion, efforts have been made to find a suitable palliative and/or curative agent for the treatment of wounds and ulcers from medicinal plants and other natural or synthetic ingredients.

Several herbal products have been proposed for the treatment of wounds and ulcers. The U.S. Pat. No. 6,133,440 to Qiu, et al., provides a rapid and efficient method for the preparation and isolation of biologically active polysaccharides from Aloe, "Immuno-10" and the use of the polysaccharides as immunostimulating, immunomodulating and wound healing agents. The U.S. Pat. No. 6,027,728 to Yuen comprises a selection of herbal materials with curative effects combined in a powdered form for application to human skin to accomplish skin regeneration, particularly for application to human skin affected with eczema, psoriasis, allergic reactions, inflammatory rash and the like. The process of application is critical to effectiveness of the present invention. The application of the herbal powder to the skin is intended to cause a temporary inflammation, which removes at least an upper skin layer, with some mild to noticeable discomfort, and causes accelerated skin regeneration so that soft, unaffected skin replaces the scaling and/or lesioned skin. The U.S. Pat. No. 5,693,327 to Shah relates to the preparation and use of compositions for the treatment of skin disorders such as psoriasis, eczema and lichen planus, as well as for the promotion of good health and the alleviation of stress. The compositions are based on extracts from the plants Melia azadirachta and/or Centratherum anthelminthicum. A variety of other herbal extracts may be included, and the compositions may take the form of a cream or ointment based on ghee, or they may be in a powdered form of suitable for preparing decoctions in hot water. The U.S. Pat. No. 5,766,614 to Yong is a new Burn Treatment Composition which provides healing to the skin of people who have received burns or are afflicted with other skin complications that require healing. The inventive device includes effective amounts of Chinese rhubarb; calcium hydroxide; sanguisorba officinalis rhizome; common camphor; coptis chinensis rhizome; phellodendron amurense bark and oldenlandia diffusa roxd. The U.S. Pat. No. 6,126,950 to Bindra, et al., relates to a formulation of herbal cream for cracked heels and palms. It is comprised of a natural wax as an emulsifier, extract of curcuma and the gum of Acacia or Colophonium or Shorea. The gum gives a synergistic effect in binding and healing the skin with natural wound healing herbal extract selected from the aqueous extracts of curcuma, neem and allantonin. This is combined with a wound healing fragrant oil. The natural wound healing herbal extract acts as a humectant and the gum gives a synergistic effect in binding the skin thereby reducing water loss from the skin. The cream spreads evenly and smoothly when applied on the affected parts, and quickens healing, restores natural suppleness and softness and also serves as an antiseptic. The U.S. Pat. No. 5,405,608 to Xu for an invention that relates to a pharmaceutical preparation mainly used for treating thermal injuries of warm-blooded mammals and human. It is composed of 3 to 15% by weight of beeswax and 85 to 97% by weight of sesame oil extract of Huangqin, Huanglian, Huangbai, earthworm and poppy capsule. Scorched in the sesame oil extract, each of Huangqin, Huanglian, Huangbai, earthworm and poppy capsule is in an amount of 2 to 10 weight percent based upon the total weight of sesame oil. This invention also relates to a process for preparing the pharmaceutical preparation and includes as its essential component, beeswax. The present invention does not make use of poppy capsule, nor does it require use of sesame oil or beeswax; the present invention contains Opuntia not included in Xu's patent and utilizes a different method for the extraction of active ingredients, viz., in alcohol versus high-heat cooking in sesame oil. It is further noteworthy that a significant population is allergic to sesame oil, which is often used as a positive control for measure allergenicity. Also, direct application of poppy capsule extract can lead to many systemic complications because of the narcotic nature of the ingredients of this herb. U.S. Pat. No. 4,837,024 describes compositions which enhance and promote the wound healing process and which comprise suspensions of the fibrous protein, collagen, and of a polysaccharide, namely a glycosaminoglycan. The glycosaminoglycan is one which exhibits chemotaxis for fibroblasts or endothelial cells; the preferred glycosaminoglycans are said to be heparin, heparan sulfate and alginate, although it should be noted that alginate is not in fact a glycosaminoglycan.

The invention described here comprises a mixture of five herbs and one animal tissue, which (four out of five herbs) are extracted by soaking in 95% Ethanol (USP grade) for a period of two weeks while stirring in closed containers and then straining and filtering the extract. Extract of soybean is obtained as a commercial product. Each extract is standardized according to its marker compound(s) and factored into final calculation of the amount of extract used for the manufacturing of final preparation. The extracts corresponding to about 1–15%, preferably 5%, of the original powdered form of the herb and animal source are mixed together in a stainless steel tank with vacuum and heating implementation and then an amount of vegetable oil, preferably canola oil, is mixed for 10 minutes. Soybean extract equivalent to yield a final added concentration of 5% of β-sitosterol is added and the preparation mixed well. Vacuum is then applied while heating the preparation to 40° C. to remove alcohol, leaving a residue of alcohol not more than one percent in the final preparation. This, however, is not a critical step. The oil mixture is then filtered through muslin cloth to remove any suspended particles. Further the while the preparation is still hot, pharmaceutical grade wax in the amount equivalent to final preparation composition of 8% is added and the mixture stirred gently for about 5 minutes at elevated temperature and then allowed to cool in appropriate containers such as laminated plastic tubes or laminated aluminum tubes or jars (laminated plastic, laminated metal or glass). The quantity of wax added is also not critical and can be adjusted to provide a consistency of ointment suitable for topical administration. Different amounts of wax can be added to produce preparations that may be useful for different purposes. For example, for lip balm, a 10% content of wax is needed while for application as diaper rash product, 7% wax is considered sufficient.

Huangqin (Scutellaria baicalensis Georgi) used in the invention is selected one or more from the group of Scutellaria viscidula Bge, Scutellaria amoena C. H. Wright, Scutellaria rehderiana Diels, Scutellaria ikonnikovii Juz, Scutellaria likiangensis Diels and Scutellaria hypericifolia Levl of Labiatae Family. The root or radix is used. (A Dictionary of Chinese Materia Medica, Shanghai Science and Technology Press, 1988, pages 2017 to 2021). It is known to have antilipidemic, anticoagulant, antithrombotic, antiallergant, vasodilatation and antibacterial properties.

Huangbo (Phellodendron amurense Rupr) used in the invention is selected from one or more groups of Phellodendron chinense Schneid, Plellodendron chinense Scheid var. glabriusculum Schneid, Phellodendron chinense Schneid var. omeiense Huang, Phellodendron Schneid var. yunnanense Huang and Phellodendron chinense Schneid var. falcutum Huang. The bark or cortex is used. (A Dictionary of Chinese Materia Medica, Shanghai Science and Technology Press, 1988, pages 2031 to 2035). Phellendori contains berberine and palmitine alkaloids, polysaccharides; it is immunosuppressive, bactericidal, antiinflammatory, bile secretion stimulant, affects gastric secretions and has antiacne properties.

Huanglian (Coptis chinensis Franch) used in the invention is selected but not limited to one or more from the group of Coptis deltoidea C. Y. Cheng et Hsiao, Coptis omeiensis (Chen) C. Y. Cheng, and Coptis teetoides C. Y. Cheng of Ranunculaceae Family. The root is used. (A Dictionary of Chinese Materia Medica, Shanghai Science and Technology Press, 1988, pages 2022 to 2030). Huanglian also contains berberine (see above).

Earthworm also called Dilong (earth dragon) is selected one or more from the group of Pheretima aspergillum (E. Perrier) and Allolobophora caliginosa trapezoides (Ant. Duges). The whole worm dried or fresh is used. (A Dictionary of Chinese Materia Medica, Shanghai Science and Technology Press, 1988, pages 2111 to 2114). It is known to have antispasmodic, antithrombotic activity.

Opuntia comprises mainly the whole plant of Opuntia ficus indica (Cactacea family) as the main constituents. Other species and varieties of Opuntia genus of the Cactaceae family are included here by reference. The reported pharmacologic properties of Opuntia include: analgesia, antiinflmmatory, antiulcerogenic, antioxidative, affecting activity of aromatase and reductase, free radical scavenger, antiviral, lowering LDL cholesterol levels, glucose-6-phosphatase and fructose-1,6-diphosphatase activity, antidiabetic, a rich source of biologically active alkaloids and other nutritional elements often considered essential for tissue growth.

Soybean extract containing a minimum of 40% β-sitosterol as used in this invention (Sigma Chemicals Catalog S5753), which also contains campesterol, dihydrobrassicacasterol prepared according to the method of N. Kozumi, et al., Chem. Pharm. Bull., 27:38, 1979. The source of β-sitosterol however is not relevant. It could be obtained from natural sources or from synthetic sources. β-sitosterol ($CH_{29}H_{50}O$, molecular weight 414.72) is a common sterol in plants. It is generally isolated from wheat germ, soybean or corn oil. Sterols are important cyclized triterpenoids that perform many critical functions in cells. Phytosterols such as campesterol, stigmasterol and β-sitosterol in plants, ergosterol in fungi and cholesterol in animals are each primary components of the cellular and sub-cellular membranes in their respective cell types. The dietary source of phytosterols in humans comes from vegetables and plant oils. The estimated daily phytosterol content in the conventional western-type diet is approximately 250 mg in contrast to a vegetable diet, which would provide double that amount. Although having no nutritional value to humans, phytosterols have recently received a great deal of attention due to their possible anti-cancer properties and their ability to decrease cholesterol levels when fed to a number of mammalian species, including humans. Phytosterols aid in limiting cholesterol absorption, enhance biliary cholesterol excretion and shift cholesterol from atherosclerotic plaque. While many of the mechanisms of action remain unknown, the relationship between cholesterol and phytosterols is apparent. This is perhaps not surprising given that chemically, phytosterols closely resemble cholesterol in structure. The major phytosterols are β-sitosterol, campesterol and stigmasterol. Others include stigmastanol (β-sitostanol), sitostanol, desmosterol, chalinasterol, poriferasterol, clionasterol and brassicasterol. (Gould R. G., Jones R. J., LeRoyu G. V., Wissler R. W., Taylor C. B.; Absorbability of B-sitosterol in humans; Metabolism, (August) 1969; 18(8): 652–662. Tabata T., Tanaka M., Lio T.; Hypocholesterolemic activity of phytosterol. II; Yakugaku Zasshi, 1980; 100(5): 546–552. Hepistall R. H., Porter K. A.; The effect of β-sitosterol on cholesterol-induced atheroma in rabbits with high blood pressure; Br. J. Experimental Pathology, 1957; 38: 49–54.). The role of phytosterols, particularly, β-sitosterol in stimulating human stem cells and particularly promoting hair growth has not been reported yet. Several novel applications of phytosterols including β-sitosterol have been reported. The U.S. Pat. No. 5,965,449 to Novak describes a method of assessing risk for cardiovascular disease and other disorders and phytosterol-based compositions useful in preventing and treating cardiovascular disease and other disorders. The level of serum campesterol and β-sitosterol are determined and their ratio is correlated with the risk of cardiovascular or a related disorder. The U.S. Pat. No. 5,523,087 to Shlyankevich is for a pharmaceutical composition for the treatment of diabetic male sexual dysfunction; it contains physosterogens, phosphatidyl choline, β-sitosterol, Damiana leaf extract and vitamins and minerals. The U.S. Pat. No. 5,486,510 to Bouic, et al., is for a mixture of β-sitosterol glucoside and β-sitosterol is administered to persons for the modulation or control of immune responses. The U.S. Pat. No. 5,747,464 to See is for a composition for inhibiting absorption of fat and cholesterol from the gut and a method for making and using the composition. The composition comprises β-sitosterol bound irreversibly to pectin to form a β-sitosterol and pectin complex. The U.S. Pat. No. 5,118,671 to Bombardelli, et al., is for complexes formed between aescin, cholesterol or β-sitosterol and phospholipids and a method for producing an anti-inflammatory effect is also described.

[Composition of a Preferred Embodiment]

| Ingredient | Composition |
| --- | --- |
| Huangbai | 5% |
| Huanglin | 5% |
| Huangqin | 5% |
| Dilong | 5% |
| Opuntia | 5% |
| β-sitosterol | 5% (from extract of soybean) |
| Canola oil | QS to 1 L |
| Alcohol USP | For extraction purpose |

It will be appreciated by those skilled in this art that the above approximate weight percentages are dependent on generally expected potencies of the components, whereby the relative weight percentages will vary sometimes substantially from the above individual amounts. It will be within the skilled person's knowledge with this disclosure that the objects of the present invention require the inclusion of each of the components in relative approximate weight percentages above. As disclosed in the prior art, individual components comprise medicinal effects on the epidermis and dermis and yield substantially absorbable molecular classes. The composition selected above acts by providing many vital functions in the healing process. From supplying appropriate nutrition, to preventing infection, to accelerating debridement and finally to enhancing stem cell growth, the invention describes here heals wounds rapidly with a much better quality of scar than obtained by other means, particularly where the wound is allowed to dry out.

The application of the pharmaceutical preparation of the invention made from purely natural ingredients. Many of the ingredients required in the formulation of preparation described above are fully characterized in the Chinese Pharmacopoeia (Pharmacopoeia of The People's Republic of China, English Edition 1994, Volume I, The Pharmacopoeia Commission of PRC, Beijing, China: Cortex Phellodendri (Huangbai)), p 33; Rhizoma Coptidis (Hunaglin), p 187; Radix Scutellariae (Hunagqin), p 170; Pheretime (Dilong), p 128) and the specifications of these ingredients are hereby included by reference in this patent application. Optunia ficus indica is not included in the Chinese Pharmacopoeia. The source material for this plant includes the entire plant including flowers, dried and powdered. Soybean is specified in the U.S. Pharmacopoeia. Canola oil is the oil from low erusic acid variety of rapeseed plant and is widely used for everyday cooking. The specifications include: free fatty acid maximum 0.05% as oleic acid, peroxide value 1.0 mEq/Kg maximum, AOM (OSI) 12 hours min to 100 mEq/Kg, iodine value 110–126. The choice of canola oil is not material to this invention. Any vegetable oil, preferably those high in natural sterols, are recommended. Wax represents any solidifying agent, which may include natural or synthetic waxes, or other ingredients that impart the preparation a consistency suitable for its specific use. The pharmaceutical preparation of the invention described here relieves pain, provides soothing effect and upon repeated use, has the ability to heal the wounds by provided a moist healing environment and stimulating stem cells to regenerate the lost tissues.

The invention described here is applied directly to open wounds, one to two times per day as a thin layer, 1–2 mm thick evenly on the surface of the wound. Reapplication of the preparation should precede with removing the older layer of ointment using a spatula or other device to remove the necrotic tissue (debridement) in the event of deeper wounds and burns. The dose application suggested here is for reference purpose only. Being an all-natural product, it is extremely safe for use in humans and a clinician or others expert in the art of treatment would readily master the art of using the preparation described here.

We studied the properties of the invention on stimulation of stem cell populations by using the technique of $^3$H-TdR (tritiated thymidine) labeling of stem cells. The effects of compositions described here were studied on explants of murine skin. Explant cultures were serially harvested at daily intervals for the first 4 days of exposure, and composition effects on $^3$H-TdR incorporation assessed in accordance with standard techniques. Because of the slow-cycling nature of stem cells, repeated administration of $^3$H-TdR is necessary. After the labeling, the cells are chased for four weeks wherein the stem cells retain the label longer and are thus quantitated comparatively to control.

In another series of experiments, a cohort of mice was continuously labeled for 2 weeks with $^3$H-TdR and then allowed to rest for 4 weeks. Once labeled, cells that cycle slowly retained isotopes for an extended period of time. Twice daily, subcutaneous injections of $^3$H-TdR were given to newborn mice over the first seven days of life resulting in the labeling of almost 100% of nuclei in mouse epidermis, hair follicles, sebaceous glands, fibroblasts, and endothelial cells. Once labeled, cells, which cycle slowly (stem cells) retain the isotope for an extended period of time and are, thus, identified as label retaining cells. Test preparations were applied dermally to labeled animals. Four hours prior to sacrifice, colcemide (4 mg/kg) was injected intraperitoneally. Animals were sacrificed at 2, 6, 12 and 24 hours after the application of composition and skin from injected areas fixed and processed for autoradiography according to routine procedures. Appearance of labeled mitotic figures indicated that slow cycling cells (stem cells) have been induced to proliferate.

What is claimed is:

1. A composition for topical medicinal application to a body surface to treat surface wounds in humans and animals free of poppy capsule consisting essentially of the following ingredients in the percentages by weight indicated;

an alcoholic extract of Huangbai 1–20% an alcoholic extract of Huanglin 1–20% an alcoholic extract of Huangqin 1–20% an alcoholic extract of Dilong 1–20% an alcoholic extract of Opuntia 1–20% an alcoholic extract of β-sitosterol 1–20%; and

Canola oil QS to Volume.

2. The composition of claim 1 wherein β-sitosterol is derived from either natural or synthetic source.

3. The composition of claim 1 wherein β-sitosterol is derived from soy extract.

4. The composition of claim 1 wherein the composition is used for the treatment of surface wounds in humans and animals including burns, stasis ulcers, cutaneous wounds, donor skin surgery wounds, chemical, mechanical, or laser peel burns, chapped lips, cracked nipples, diaper rash, severe cuts, abrasions, sunburn, diabetic ulcers, trophic lesions, wherein the tropic lesions are selected from the group consisting of decubitus ulcers, allergic ulcers, dehiscence wounds, acral lick dermatitis, acral lick granulomas in animals, lacerations, and wounds that are traumatic in origin.

5. The composition of claim 1 wherein the composition stimulates the dormant basal stem cells and thus regenerates the dermal and epidermal cells producing the healing effect.

* * * * *